United States Patent
Seo et al.

(10) Patent No.: US 9,417,180 B2
(45) Date of Patent: Aug. 16, 2016

(54) OPTICAL MEASURING METHODS AND SYSTEM

(71) Applicant: Samsung Electronics Co., Ltd., Suwon-si (KR)

(72) Inventors: Dong-Min Seo, Hwaseong-si (KR); Jang-Ik Park, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 14/601,407

(22) Filed: Jan. 21, 2015

(65) Prior Publication Data

US 2015/0362367 A1 Dec. 17, 2015

(30) Foreign Application Priority Data

Jun. 13, 2014 (KR) .................. 10-2014-0072337

(51) Int. Cl.
*G01J 1/10* (2006.01)
*G01N 21/21* (2006.01)

(52) U.S. Cl.
CPC ........ *G01N 21/211* (2013.01); *G01N 2021/213* (2013.01)

(58) Field of Classification Search
CPC . G03F 9/7019; G01F 7/70516; G01B 21/042; G01N 2021/213; G01N 21/211; G01N 21/274
USPC ................... 356/601–623, 369, 445–448, 356/237.1–237.5, 243.1, 243.4, 243.8; 702/85, 90, 97, 41, 175, 108; 250/252.1
See application file for complete search history.

(56) References Cited

U.S. PATENT DOCUMENTS

| | | | |
|---|---|---|---|
| 5,489,980 A | 2/1996 | Anthony | |
| 6,153,444 A * | 11/2000 | Nakano | G01R 31/2656 257/E21.53 |
| 6,366,861 B1 | 4/2002 | Waldhauer et al. | |
| 6,532,428 B1 * | 3/2003 | Toprac | H01L 22/20 257/E21.525 |
| 6,770,868 B1 * | 8/2004 | Bevis | G01B 15/04 250/252.1 |
| 6,891,158 B2 | 5/2005 | Larson et al. | |
| 6,912,056 B2 | 6/2005 | Hyun et al. | |
| 7,273,685 B2 | 9/2007 | Sasazawa et al. | |
| 7,678,588 B2 | 3/2010 | Huang et al. | |
| 8,199,336 B2 | 6/2012 | Nabatova-Gabain et al. | |
| 8,582,124 B2 | 11/2013 | Yamazaki et al. | |
| 2006/0170921 A1 * | 8/2006 | Oka | G01J 4/04 356/364 |
| 2006/0274306 A1 * | 12/2006 | Hasan | H01L 21/67276 356/237.5 |
| 2007/0201017 A1 * | 8/2007 | Opsal | G01B 11/0641 356/237.2 |
| 2011/0292365 A1 * | 12/2011 | Cramer | G01N 21/4785 355/67 |
| 2013/0151440 A1 * | 6/2013 | Li | G01N 21/956 706/12 |
| 2015/0029517 A1 * | 1/2015 | Park | G01B 11/0633 356/630 |
| 2015/0369664 A1 * | 12/2015 | Garsha | G01J 3/10 356/402 |

FOREIGN PATENT DOCUMENTS

| KR | 10-2007-0044273 A | 4/2007 |
|---|---|---|
| KR | 10-2007-0077260 A | 7/2007 |

(Continued)

*Primary Examiner* — Hoa Pham
(74) *Attorney, Agent, or Firm* — Myers Bigel & Sibley (57) ABSTRACT

In an optical measuring method, a reflected light from a structure on a substrate is detected by a measuring tool to obtain a raw spectrum. The raw spectrum in a wavelength range having spectrum sensitivity to process variation is analyzed to determine a process variation of an actual process performed on the substrate. The raw spectrum is corrected according to a spectrum offset for the measuring tool which is determined based on the process variation.

20 Claims, 4 Drawing Sheets

(56) References Cited

FOREIGN PATENT DOCUMENTS

| | | |
|---|---|---|
| KR | 10-2007-0077618 A | 7/2007 |
| KR | 10-2007-0113655 A | 11/2007 |
| KR | 10-2012-0122759 A | 11/2012 |
| KR | 10-2012-0134493 A | 12/2012 |

* cited by examiner

OPTICAL MEASURING METHODS AND SYSTEM

PRIORITY STATEMENT

This application claims priority under 35 U.S.C. §119 to Korean Patent Application No. 10-2014-0072337, filed Jun. 13, 2014 in the Korean Intellectual Property Office (KIPO), the contents of which are hereby incorporated herein by reference in its entirety.

FIELD

Example embodiments relate to an optical measuring method and an optical measuring system. More particularly, example embodiments relate to an optical measuring method of measuring characteristics of wafer and an optical measuring system for performing the same.

BACKGROUND

In semiconductor manufacturing, optical metrology is typically used for measuring and evaluating properties such as optical properties, shapes of nano patterns, and the like, of nano samples in real time by a non-destructive manner or a non-contact manner. For example, after a periodic grating is formed on a semiconductor wafer, an optical metrology system may be used to determine a profile of the periodic grating.

For example, after a plurality of wafers is sequentially loaded into one semiconductor manufacturing apparatus, a specific semiconductor process may be performed on the wafers respectively. Some wafers sampled from the wafers processed by the processes may be measured by different measuring tools.

Because the sampling wafers may be measured in a defined order by several measuring tools, not by one measuring tool, an error between measurement values may occur due to variations in optical components and light beam profiles between the measuring tools. In order to compensate the error by the tool variation, final data may be corrected by an offset. However, because the final data may include an error caused by the tool variation as well as process variation, even though the final data is corrected by the offset, the error may not be completely compensated.

SUMMARY

Example embodiments provide an optical measuring method capable of compensating for an error caused by variation in optical measuring tools.

Example embodiments provide an optical measuring system for performing the optical measuring method.

According to example embodiments, in an optical measuring method, a reflected light from a structure on a substrate is detected by a measuring tool to obtain a raw spectrum. The raw spectrum in a wavelength range having spectrum sensitivity to process variation is analyzed to determine a process variation of an actual process performed on the substrate. The raw spectrum is corrected according to a spectrum offset for the measuring tool which is determined based on the process variation.

In example embodiments, obtaining the raw spectrum may include obtaining an amplitude ratio ($\tan(\Psi)$) or phase difference ($\Delta$) spectrum of the reflected light using spectroscopic ellipsometry.

In example embodiments, the raw spectrum in the wavelength range may represent the process variation between an actual process and a reference process, and in the wavelength range, spectrum sensitivity to process variation may be greater than spectrum sensitivity to tool variation.

In example embodiments, the spectrum offset for the measuring tool may be determined as a difference of the spectrum of the measuring tool with reference to the spectrum of reference tool or a difference of the spectrum of the measuring tool with reference to the average spectrum for all measuring tools.

In example embodiments, the method may further include calculating a profile of the structure from the corrected spectrum using a modeling technique.

In example embodiments, the method may further include using the calculated profile of the structure to perform a process control.

In example embodiments, the profile of the structure may include a thickness of the structure.

In example embodiments, the structure may include a periodic grating.

According to example embodiments, in an optical measuring method, raw spectrums are obtained from a plurality of substrates by measuring tools respectively. The raw spectrums in a wavelength range where spectrum sensitivity to process variation is greater than spectrum sensitivity to tool variation are analyzed to determine process variations between processes performed on the substrates. A spectrum offset for each of the measuring tools is determined based on the process variations. The raw spectrum is corrected according to the spectrum offset.

In example embodiments, obtaining the raw spectrum may include obtaining an amplitude ratio ($\tan(\Psi)$) or phase difference ($\Delta$) spectrum of a reflected light from a structure on the substrate using spectroscopic ellipsometry.

In example embodiments, the method may further include analyzing the spectrums representing the process variations to determine a spectrum of reference process, after determining the process variations between the processes performed on the substrates.

In example embodiments, the method may further include analyzing the spectrums for the measuring tools in the reference process to determine a spectrum of reference tool.

In example embodiments, determining the spectrum offset for the measuring tool may include determining a difference of the spectrum of the measuring tool with reference to the spectrum of reference tool or a difference of the spectrum of the measuring tool with reference to the average spectrum for all measuring tools as the spectrum offset.

In example embodiments, the method may further include calculating a profile of a structure on the substrate from the corrected spectrum using a modeling technique.

In example embodiments, the method may further comprise using the calculated profile of the structure to perform a process control.

According to example embodiments, an optical measuring system includes an optical measuring equipment installed in a manufacturing process line and having a plurality of measuring tools, wherein the measuring tool irradiates a light onto a substrate having a structure formed by a manufacturing process and detects a reflected light to provide a raw spectrum, and a data correction device connected to the optical measuring equipment, and analyze the raw spectrum in a wavelength range having spectrum sensitivity to process variation and spectrum sensitivity to tool variation to correct an error between the measuring tools.

In example embodiments, the measuring tool may include a spectroscopic ellipsometer as a light detector, and the measuring tool may obtain an amplitude ratio (tan(Ψ)) spectrum or phase difference (Δ) spectrum of the reflected light from the structure on the substrate.

In example embodiments, the data correction device may include an analyzer configured to analyze the raw spectrums in the wavelength range where spectrum sensitivity to process variation is greater than spectrum sensitivity to tool variation to determine process variations between the processes performed on the substrates, and a corrector configured to determine a spectrum offset for each of the measuring tools based on the process variations and correcting the raw spectrums according to the spectrum offset.

In example embodiments, the analyzer may analyze the spectrums representing the process variations to determine a spectrum of reference process and may analyze the spectrums for the measuring tools in the reference process to determine a spectrum of reference tool.

In example embodiments, the corrector may determine the spectrum offset for the measuring tool comprising determining a difference of the spectrum of the measuring tool with reference to the spectrum of reference tool or a difference of the spectrum of the measuring tool with reference to the average spectrum for all measuring tools as the spectrum offset.

According to example embodiments, raw spectrums may be obtained from sampling wafers by optical measuring tools, and then, the raw spectrums in a wavelength range where spectrum sensitivity to process variation is relatively greater than spectrum sensitivity to tool variation may be analyzed to determine a process variation in the process which had been performed on the wafer. Then, after a spectrum offset for each of the measuring tools is applied to correct the raw spectrum, the corrected spectrum may be used to calculate a profile of a structure formed on the wafer.

Accordingly, a spectrum difference by process variation may be determined in the raw spectrum, and then, the spectrum offset for each measuring tool may be calculated to correct the raw spectrum. Thus, the raw spectrum may be corrected and the corrected spectrum may be used to compensate errors between different tools, without correcting final data.

BRIEF DESCRIPTION OF THE DRAWINGS

Example embodiments will be more clearly understood from the following detailed description taken in conjunction with the accompanying drawings. FIGS. 1 to 5 represent non-limiting, example embodiments as described herein.

DETAILED DESCRIPTION OF EXAMPLE EMBODIMENTS

Various example embodiments will be described more fully hereinafter with reference to the accompanying drawings, in which example embodiments are shown. Example embodiments may, however, be embodied in many different forms and should not be construed as limited to example embodiments set forth herein. Rather, these example embodiments are provided so that this disclosure will be thorough and complete, and will fully convey the scope of example embodiments to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, example embodiments will be explained in detail with reference to the accompanying drawings.

Figure 1:
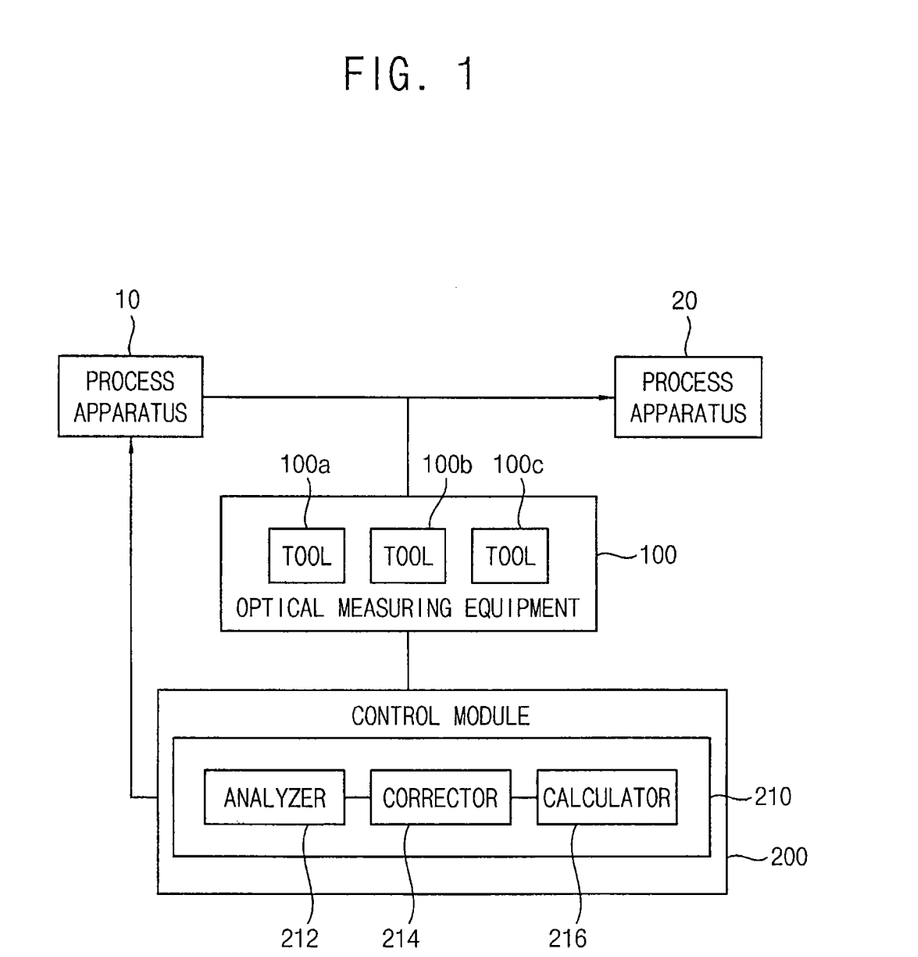
FIG. 1 is a block diagram illustrating an optical measuring system in accordance with example embodiments.
Figure 2:
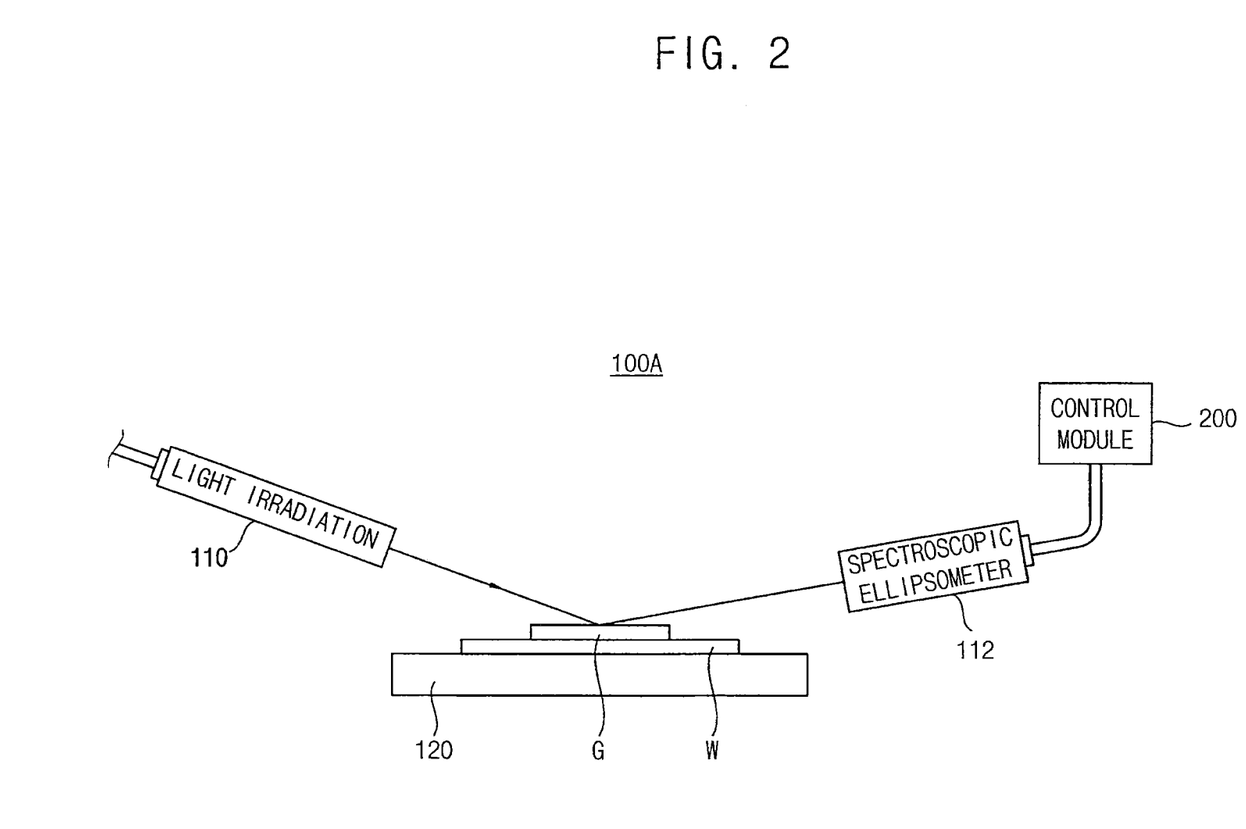
FIG. 2 is a block diagram illustrating a measuring tool in FIG. 1.
Figure 3:
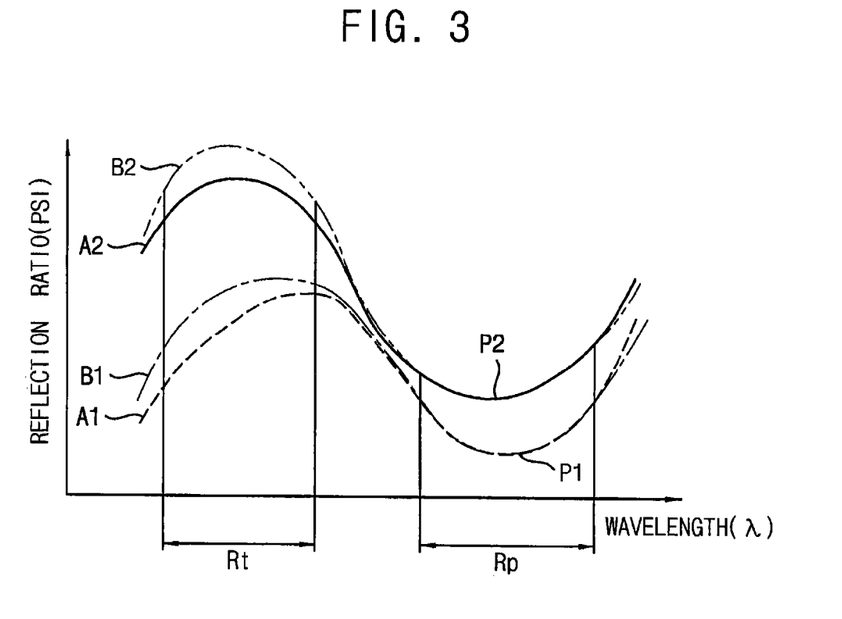
FIG. 3 is a graph illustrating measurement spectrums obtained by the measuring tools in FIG. 1.
Figure 4:
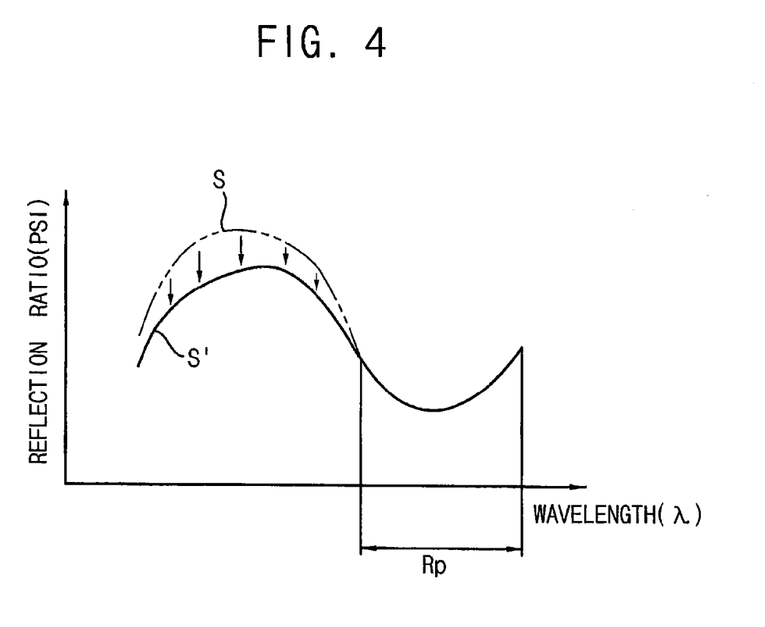
FIG. 4 is a graph illustrating a process of calibrating a measurement spectrum in accordance with example embodiments.

FIG. 1 is a block diagram illustrating an optical measuring system in accordance with example embodiments. FIG. 2 is a block diagram illustrating a measuring tool in FIG. 1. FIG. 3 is a graph illustrating measurement spectrums obtained by the measuring tools in FIG. 1. FIG. 4 is a graph illustrating a process of calibrating a measurement spectrum in accordance with example embodiments.

Referring to FIGS. 1 to 4, an optical measuring system may include optical measuring equipment 100 having a plurality of measuring tools 100a, 100b, 100c installed in a manufacturing process line to measure a substrate, and a data correction device 210 for correcting measurement data obtained by the measuring tools in order to compensate for errors between the measuring tools.

In example embodiments, an optical measuring system may be used to monitor a semiconductor process for forming semiconductor devices such as DRAM, VNAND, etc through non-destructive testing.

As illustrated in FIG. 1, a substrate such as a semiconductor wafer may be sequentially processed by process apparatuses 10 and 20 to form a semiconductor device. For example, the process apparatuses 10 and 20 may include any appropriate process apparatus generally known in the art of semiconductor manufacturing such as a lithography apparatus, an etch apparatus, a deposition apparatus, etc.

The wafer may refer to a substrate formed of a semiconductor or non-semiconductor material. The wafer may include one or more layers formed on the substrate. For example, such layers may include, but are not limited to, a resist, a dielectric material or a conductive material. Additionally, the wafer may include a plurality of dies, each having a repeatable pattern features.

In example embodiments, a plurality of wafers may be sequentially by a first process apparatus 10 and a second process apparatus 20. After a wafer is processes by the first process apparatus 10, one or more characteristics of the wafer may be measured by the optical measuring system 100. Then, the measured wafer may be processed by the second process apparatus 20. For example, the first process apparatus 10 may include a deposition apparatus and the second process apparatus 20 may include an etching apparatus.

The optical measuring equipment 100 may include a plurality of the measuring tools 100A, 100B, 100C. For example, the measuring equipment 100 may include a first measuring tool 100A, a second measuring tool 100B and a third measuring tool 100C. However, the number of the measuring tools may not be limited thereto.

The optical measuring equipment may measure only some wafers sampled from the wafers processed by the first process apparatus 10. One or more characteristics of one sampling wafer may be measured by any one selected from the first to third measuring tools 100A, 100B, 100C. That is, the sampling wafers may be measured by the first to third measuring tools 100A, 100B, 100C, respectively. The number of the sampling wafers may be determined in consideration of the overall throughput of semiconductor fabrication processes. Additionally, the measurements may be performed at only one location or a limited number of locations on the wafer, in consideration of the cycle time and the throughput of the processes.

For example, first sampling wafers $W_{3k-2}$ (k is a natural number) may be the first measuring tool 100A respectively. Second sampling wafers $W_{3k-1}$ (k is a natural number) may be the second measuring tool 100B respectively. Third sampling wafers $W_{3k}$ (k is a natural number) may be the third measuring tool 100C respectively.

The measuring tool may measure properties such as thickness of a thin layer and profile of a grating structure formed on the wafer. For example, the profile of the grating structure may include a width, a height, a sidewall angle, etc. The measuring tool may include a measuring instrument such as spectroscopic ellipsometry (SE). Alternatively, the measuring tool may include a measuring instruments such as atomic force microscopy (AFM) or scanning probe microscopy (SPM) to measure properties such as surface roughness of a layer formed on the wafer.

As illustrated in FIG. 2, in example embodiments, the first to third measuring tools 100A, 100B, 100C may include a spectroscopic ellipsometer 112. In this case, a sampling wafer W may be supported on a stage 120, and then, light from a light irradiation portion 110 may be incident upon a structure G of the wafer W. Then, a reflected light from the wafer W may be detected using the spectroscopic ellipsometer 112 to obtain a raw spectrum such as measurement data. For example, the spectroscopic ellipsometer 112 may generate a reflection ratio spectrum of s and p components into which the light incident upon the wafer is decomposed, that is, amplitude ratio ($\tan(\Psi)$) spectrum and/or phase difference ($\Delta$) spectrum.

In example embodiments, a control module 200 may be connected to the first to third measuring tools 100A, 100B, 100C of the optical measuring equipment 100. The control module 200 may include the data correction device 210 for correcting measured data obtained by the measuring tools in order to compensate for errors between the measuring tools.

The control module 200 may be connected to the measuring tools via data transmission media including cable transmission link and/or wireless transmission link The control module 200 may receive the measurement data (raw spectrums) that are generated by the measuring tools. Additionally, the control module 200 may include a computer system. The computer system may be broadly defined to encompass any device having one or more processors, which execute instructions from a memory medium.

The data correction device 210 may include an analyzer 212 for analyzing the raw spectrum provided as the measurement data and a corrector 214 for correcting the raw spectrum according to the analysis result.

The analyzer 212 may analyze the raw spectrums in a wavelength range where spectrum sensitivity to process variation is greater than spectrum sensitivity to tool variation and determine process variations between the processes performed on the wafers.

As illustrated in FIG. 3, wafers, on which a first process P1 and a second process P2 are performed respectively by the first process apparatus 10, may be measured by the first and second measuring tools 100A, 100B, respectively to obtain raw spectrums. The raw spectrum may be a measurement spectrum that is detected from a layer on the wafer. The raw spectrum may be amplitude ratio (Ψ) spectrum or phase difference (Δ) spectrum.

The wafers, on which the first process P1 is performed, may be measured by the first measuring tool 100A to obtain a raw spectrum A1 and may be measured by the second measuring tool 100B to obtain a raw spectrum B1. The wafers, on which the second process P2 is performed, may be measured by the first measuring tool 100A to obtain a raw spectrum A2 and may be measured by the second measuring tool 100B to obtain a raw spectrum B2.

Accordingly, the raw spectrum obtained from the wafer may be affected by the variation between the measuring tools and the variation between the processes performed on the wafers.

The analyzer 212 may analyze the raw spectrums to determine a first wavelength range Rp having a relatively large spectrum variation with respect to process variation. Because the spectrum sensitivity to process variation is greater than the spectrum sensitivity to tool variation in the first wavelength range Rp, the raw spectrums in the first wavelength range Rp may represent precisely a state of an actual process processed on the wafer. Accordingly, the raw spectrums A1 and B1 may be substantially identical to each other in the first wavelength range Rp and the raw spectrums A2 and B2 may be substantially identical to each other in the first wavelength range Rp. In contrast, because both the spectrum sensitivity to process variation and the spectrum sensitivity to variation are dominant in a second wavelength range Rt, the raw spectrums A1 and B1 may be different from each other in the second wavelength range Rt and the raw spectrums A2 and B2 may be different from each other in the second wavelength range Rt.

The raw spectrums in the first wavelength range Rp may be analyzed to precisely determine variations between the processes performed respectively on the wafers without being affected by variations between the first and second measuring tools 100A and 100B. That is, the raw spectrums in the wavelength range where the raw spectrum is affected mainly by the process variation and is not affected by the tool variation may be analyzed to determine a process variation of an actual process processed on the wafer.

Thus, the analyzer 212 may analyze the raw spectrums in the first wavelength range Rp to determine which process had been performed on the wafer. In FIG. 3, it may be determined that the raw spectrums A1 and B1 are obtained from the wafers on which the first process P1 had been performed and the raw spectrums A2 and B2 are obtained from the wafers on which the second process P2 had been performed.

In example embodiments, the analyzer 212 may find a reference wavelength range Rp where spectrum sensitivity to process variation is greater than spectrum sensitivity to tool variation, analyze raw spectrums in the reference wavelength range Rp, and determine which process had been performed on a wafer corresponding to each raw spectrum. The analyzer 212 may analyze variation between the raw spectrums by the same process, a difference between the raw spectrums caused by the variation between the different measuring tools in the same process.

For example, the analyzer 212 may analyze the spectrums representing the process variations to determine a spectrum of reference process, and analyze the spectrums for the measuring tools in the reference process to determine a spectrum of reference tool.

In FIG. 3, the spectrum of reference process may be selected from the raw spectrums A1 and B1 representing the first process P1 and the raw spectrums A2 and B2 representing the second process P2 in the first wavelength range Rp. For example, the first process P1 may be determined as a reference process (or representative process), and the raw spectrums A1 and B2 representing the first process P1 may be selected as the spectrum of reference spectrum.

Additionally, a reference tool may be determined from the first to third measuring tools 100A, 100B and 100C, and the spectrum of reference tool may be selected from the spectrums for the measuring tools.

In FIG. 3, after analyzing the raw spectrums in the first and second wavelength ranges Rp and Rt, the first measuring tool 100A may be selected from the first and second measuring tools 100A and 100B to be determined as a reference tool, and the raw spectrum A1 for the first measuring tool 100A may be selected as the spectrum of reference tool.

Alternatively, the average spectrum for all measuring tools 100A, 100B and 100C in the same process may be determined as a spectrum of reference tool.

In example embodiments, the corrector 214 may determine a spectrum offset for each of the measuring tools based on the process variations, and correct the raw spectrums according to the determined spectrum offset. The spectrum offset for the measuring tool may represent a difference value in the raw spectrum caused by tool variation even though in the same process.

For example, the spectrum offset for the measuring tool may be a difference of the spectrum of the measuring tool with reference to the spectrum of reference tool or a difference of the spectrum of the measuring tool with reference to the average spectrum for all measuring tools.

The spectrum offsets by various process variations may be calculated using a distribution of the processes and a distribution of the measured locations across the wafer. A reference process may be selected, and then, the spectrum offset for measuring tool may be calculated in the selected reference process. A plurality of the reference processes may be determined, and the spectrum offset between the reference processes may be calculated by interpolation.

As illustrated in FIG. 4, a raw spectrum S may be obtained from a sampled wafer by any one of the first to third measuring tools 100A, 100B and 100C. A part of the raw spectrum S in the wavelength range Rp having relatively great spectrum sensitivity to process variation may be analyzed to determine a variation of a process which had been performed on the measured wafer. A spectrum offset (for example, a difference of the actual measuring tool with reference to the spectrum of reference tool) may be calculated in the determined process, and then, a correction spectrum S' may be determined according to the spectrum offset.

In example embodiments, the data correction device 210 may further include a calculator 216. The calculator 216 may use a modeling technique from the corrected spectrum to calculate a dimensional parameter of a structure on the wafer.

The calculator 216 may use the modeling technique such as rigorous coupled wave analysis (RCWA), to calculate a profile (e.g., width, height, sidewall angle, etc) of a grating structure formed on the wafer.

In example embodiments, after the measurement values of the characteristics of the wafer are calculated, the measurement values may be used for process control (e.g., statistical process control, SPC).

The control module 200 may analyze information about the calculated characteristics of the wafers and evaluate performances of the processes performed by the first process apparatus 10. If the characteristics of the wafers are unacceptable (e.g., out of a predetermined range for the characteristic), one or more parameters of the process may be altered such that additional wafers manufactured by the process have acceptable characteristics.

For example, the control module 200 may plot the measured values of the characteristics of the wafers in SPC chart. The SPC chart may illustrate the value of the characteristics of the wafer as a function of the measurements number or measurement time, and also show the upper control level (UCL) and the lower control level (LCL). Accordingly, the SPC chart may be used to visually monitor the variation in the process performed on the wafer.

As mentioned above, after raw spectrums are obtained from sampling wafers by optical measuring tools, the raw spectrums in a wavelength range where spectrum sensitivity to process variation is relatively greater than spectrum sensitivity to tool variation may be analyzed to determine a process variation in the process which had been performed on the wafer. Then, after a spectrum offset for each of the measuring tools is applied to correct the raw spectrum, the corrected spectrum may be used to calculate a profile of a structure formed on the wafer.

Accordingly, a spectrum difference by process variation may be determined in the raw spectrum, and then, the spectrum offset for each measuring tool may be calculated to correct the raw spectrum. Thus, the raw spectrum may be corrected and the corrected spectrum may be used to compensate errors between different tools, without correcting final data.

Hereinafter, a method of measuring a dimensional parameter of a structure on a wafer using the optical measuring system will be explained.

Figure 5:
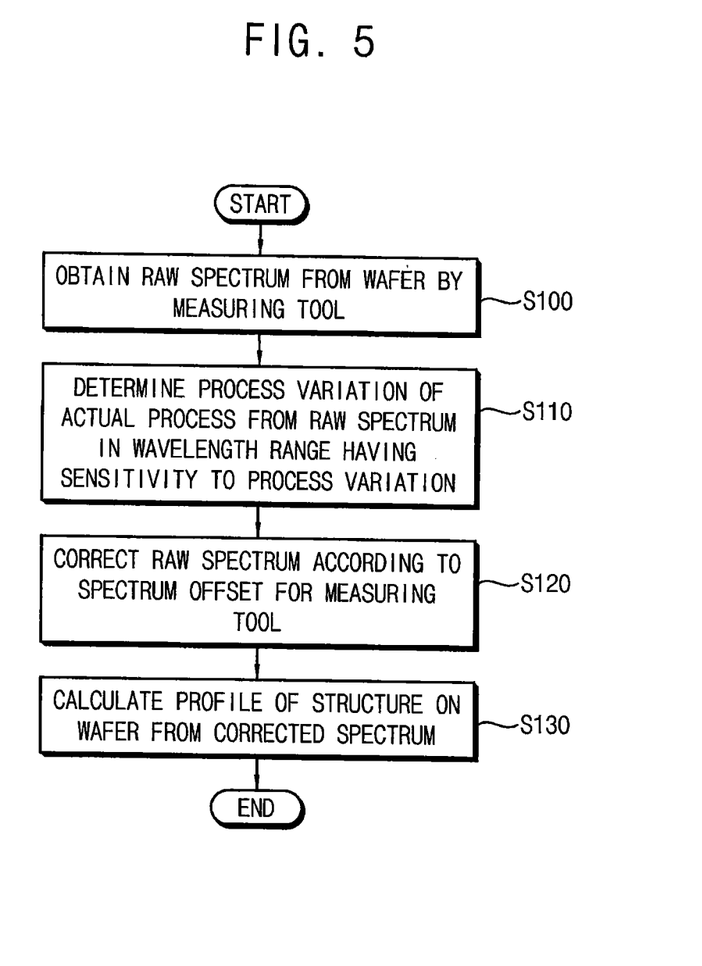
FIG. 5 is a flow chart illustrating an optical measuring method in accordance with example embodiments.

FIG. 5 is a flow chart illustrating an optical measuring method in accordance with example embodiments.

Referring to FIGS. 1, 2 and 5, first, a semiconductor manufacturing process may be sequentially performed on a plurality of wafers W, each having, a grating structure or a material layer formed thereon, by a first process apparatus 10. Then, the wafers W may be measured respectively by measuring tools 100A, 100B and 100C to obtain raw spectrums (S100).

In example embodiments, the wafers W may be sequentially loaded into a stage 120 of each of different measuring tools 100A, 100B and 100C. A reflected light from the wafer W may be detected using a spectroscopic ellipsometry 112 of the measuring tool to obtain the raw spectrum.

Then, the raw spectrums in a wavelength range where spectrum sensitivity to process variation is greater than spectrum sensitivity to tool variation may be analyzed to determine process variations between the processes performed on the wafers (S110).

The raw spectrums may be affected by the variation between the measuring tools and the variation between the processes performed on the wafers. In a specific wavelength range, the raw spectrum may be varied relatively sensitive to process variation but may be varied relatively insensitive to tool variation. The spectrum in the wavelength range where spectrum sensitivity to process variation is greater than spectrum sensitivity to tool variation first wavelength range Rp may represent precisely a state of an actual process processed on the wafer. Accordingly, the raw spectrum in the wavelength range having relatively great spectrum sensitivity to process variation may be analyzed to determine the process variation of the actual process which had been performed on the wafer.

In example embodiments, the spectrums representing the process variations may be analyzed to determine a spectrum of reference process, and the spectrums for the measuring tools in the reference process may be analyzed to determine a spectrum of reference tool. Additionally, a difference between the raw spectrums caused by tool variation in the same process may be determined.

The spectrum of reference process may be selected from the raw spectrums representing a first process and the raw spectrums representing a second process in the wavelength range. For example, the first process may be determined as a reference process (or representative process), and the raw spectrums representing the first process may be selected as the spectrum of reference spectrum.

Additionally, the raw spectrums representing the same process may be analyzed to determine one of the measuring tools as a reference tool, and determine one of the spectrums for the measuring tools as the spectrum of reference tool. Alternatively, the average spectrum for all measuring tools in the same process may be determined as the spectrum of reference tool.

Then, a spectrum offset for each of the measuring tools may be determined based on the process variations, and then the raw spectrum may be corrected according to the spectrum offset (S120).

The spectrum offset for the measuring tool may be a difference of the spectrum of the measuring tool with reference to the spectrum of reference tool or a difference of the spectrum of the measuring tool with reference to the average spectrum for all measuring tools.

Then, a dimensional parameter of a structure on the wafer may be calculated from the corrected spectrum using a modeling technique (S130).

For example, a modeling technique such as rigorous coupled wave analysis (RCWA) may be used to calculate a profile (e.g., width, height, sidewall angle, etc) of a grating structure formed on the wafer.

Then, the calculated profile of the structure may be used to perform a process control.

After the measurement values of the characteristics of the wafer are calculated, the measurement values may be used for process control (e.g., statistical process control, SPC). Information about the calculated characteristics of the wafers may be analyzed to evaluate performances of the processes performed by the process apparatus. If the characteristics of the wafers are unacceptable (e.g., out of a predetermined range for the characteristic), one or more parameters of the process may be altered such that additional wafers manufactured by the process have acceptable characteristics.

Semiconductor devices such as DRAM, VNAND, etc., manufactured using the optical measuring method and optical measuring system may be used in conjunction with various systems such as a computing system. The system may be applied to computer, portable computer, laptop computer, PDA, tablet, mobile phone, digital music player, etc.

The foregoing is illustrative of example embodiments and is not to be construed as limiting thereof. Although a few example embodiments have been described, those skilled in the art will readily appreciate that many modifications are possible in example embodiments without materially departing from the novel teachings and advantages of the present invention. Accordingly, all such modifications are intended to be included within the scope of example embodiments as defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. An optical measuring method, comprising:
   detecting a reflected light from a structure on a substrate by a measuring tool to obtain a raw spectrum;
   analyzing the raw spectrum to determine a wavelength range having spectrum sensitivity to process variation that is greater than spectrum sensitivity to tool variation;
   analyzing the raw spectrum in the wavelength range to determine a process variation of an actual process performed on the substrate; and
   correcting the raw spectrum according to a spectrum offset for the measuring tool which is determined based on the process variation.

2. The method of claim 1, wherein obtaining the raw spectrum comprises obtaining an amplitude ratio ($\tan(\Psi)$) or phase difference ($\Delta$) spectrum of the reflected light using spectroscopic ellipsometry.

3. The method of claim 1, wherein the raw spectrum in the wavelength range represents the process variation between the actual process and a reference process.

4. The method of claim 1, wherein the spectrum offset for the measuring tool is determined as a difference of a spectrum of the measuring tool with reference to a spectrum of a reference tool or a difference of the spectrum of the measuring tool with reference to an average spectrum for a plurality of measuring tools.

5. The method of claim 1, further comprising calculating a profile of the structure from the corrected spectrum using a modeling technique.

6. The method of claim 5, further comprising using the calculated profile of the structure to perform a process control.

7. The method of claim 5, wherein the profile of the structure comprises a thickness of the structure.

8. The method of claim 1, wherein the structure comprises a periodic grating.

9. An optical measuring method, comprising:
   obtaining raw spectrums from a plurality of substrates by respective measuring tools;
   analyzing the raw spectrums to determine a wavelength range having spectrum sensitivity to process variation that is greater than spectrum sensitivity to tool variation;
   analyzing the raw spectrums in the wavelength range to determine process variations between processes performed on the substrates;
   determining a spectrum offset for each of the measuring tools based on the process variations; and
   correcting the raw spectrums according to the respective spectrum offsets.

10. The method of claim 9, wherein obtaining each raw spectrum comprises obtaining an amplitude ratio ($\tan(\Psi)$) or phase difference ($\Delta$) spectrum of a reflected light from a structure on the substrate using spectroscopic ellipsometry.

11. The method of claim 9, further comprising analyzing the spectrums representing the process variations to determine a spectrum of a reference process, after determining the process variations between the processes performed on the substrates.

12. The method of claim 11, further comprising analyzing the spectrums for the measuring tools in the reference process to determine a spectrum of a reference tool.

13. The method of claim 12, wherein determining the spectrum offset for the measuring tool comprises determining a difference of the spectrum of the measuring tool with reference to the spectrum of the reference tool or a difference of the spectrum of the measuring tool with reference to an average spectrum for all of the measuring tools as the spectrum offset.

14. The method of claim 9, further comprising calculating a profile of a structure on one of the substrates from the respective corrected spectrum using a modeling technique.

15. The method of claim 14, further comprising using the calculated profile of the structure to perform a process control.

16. An optical measuring system, comprising:
   an optical measuring tool configured to detect reflected light from a structure on a substrate to obtain a raw spectrum; and
   a control module configured to analyze the raw spectrum to determine a wavelength range having spectrum sensitivity to process variation that is greater than spectrum sensitivity to tool variation, to analyze the raw spectrum in the wavelength range to determine a process variation of an actual process performed on the substrate, and to produce a corrected spectrum according to a spectrum offset for the measuring tool which is determined based on the process variation.

17. The system of claim 16, wherein the optical measuring tool comprises a spectroscopic ellipsometer that is configured to generate a reflection ratio spectrum of components into which light incident upon the substrate is decomposed.

18. The system of claim 16, wherein the control module comprises a calculator configured to calculate a profile of the structure from the corrected spectrum using a modeling technique.

19. The system of claim 18, wherein the modeling technique comprises a rigorous coupled wave analysis (RCWA).

20. The system of claim 18, wherein the control module is configured to utilize the profile of the structure for process control.

* * * * *